United States Patent
Fukuyama et al.

(10) Patent No.: US 10,481,163 B1
(45) Date of Patent: Nov. 19, 2019

(54) MASS SPECTROMETRY METHOD USING MIXED MATRIX

(71) Applicant: SHIMADZU CORPORATION, Kyoto-shi, Kyoto (JP)

(72) Inventors: Yuko Fukuyama, Kyoto (JP); Koichi Tanaka, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/993,742

(22) Filed: May 31, 2018

(51) Int. Cl.
| | |
|---|---|
| H01J 49/26 | (2006.01) |
| H01J 49/00 | (2006.01) |
| G01N 33/68 | (2006.01) |
| H01J 49/16 | (2006.01) |

(52) U.S. Cl.
CPC ...... *G01N 33/6851* (2013.01); *H01J 49/0027* (2013.01); *H01J 49/164* (2013.01)

(58) Field of Classification Search
CPC ....... H01J 49/26; H01J 49/0027; H01J 49/164
USPC .................................. 250/281, 282, 288
See application file for complete search history.

(56) References Cited

U.S. PATENT DOCUMENTS

| | | | |
|---|---|---|---|
| 9,453,846 B2* | 9/2016 | Fukuyama | G01N 27/62 |
| 9,885,725 B2* | 2/2018 | Fukuyama | G01N 33/6851 |
| 2005/0224710 A1 | 10/2005 | Matsuo et al. | |
| 2006/0240562 A1 | 10/2006 | Caprioli et al. | |
| 2007/0075241 A1 | 4/2007 | Kim | |

(Continued)

FOREIGN PATENT DOCUMENTS

| | | |
|---|---|---|
| JP | 2005-326391 A | 11/2005 |
| JP | 2013-134102 A | 7/2013 |
| JP | 2013137294 A | 7/2013 |
| JP | 2013-164382 A | 8/2013 |
| JP | 2013-190250 A | 9/2013 |

(Continued)

OTHER PUBLICATIONS

Communication dated Nov. 20, 2018 from the Japanese Patent Office in counterpart application No. 2015-229219.

(Continued)

*Primary Examiner* — Nicole M Ippolito
(74) *Attorney, Agent, or Firm* — Sughrue Mion, PLLC (57) ABSTRACT

The present invention provides a mass spectrometry method using a mixed matrix, capable of easily and efficiently improving the ionization efficiency in mass spectrometry for peptides having a wide range of degrees of hydrophobicity (from hydrophilic to hydrophobic). A MALDI mass spectrometry method for analyzing a sample using as a mixed matrix, 2,4,6-trihydroxyalkylphenone represented by the following general formula (I):

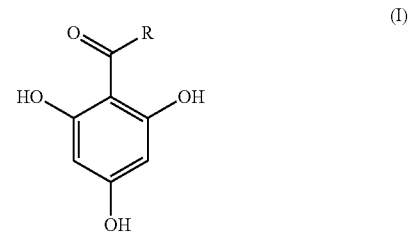

wherein R represents an alkyl group having 3 to 12 carbon atoms, and a matrix (II) for mass spectrometry that is more hydrophilic than 2,4,6-trihydroxyalkylphenone represented by the formula (I) wherein R is an alkyl group having 3 carbon atoms.

7 Claims, 3 Drawing Sheets

Specification includes a Sequence Listing.

| | Hydrophobic peptide NF-kB inhibitor (SSRCalc: 54.76) | Hydrophilic peptide Amyloid β 1-11 (SSRCalc: 13.47) |
|---|---|---|
| C8-ATHAP+4-CHCA (10+1) | | |
| C8-ATHAP | | ND |
| 4-CHCA | | |

(56) References Cited

U.S. PATENT DOCUMENTS

| | | | |
|---|---|---|---|
| 2009/0269855 A1 | 10/2009 | Wang et al. | |
| 2011/0207227 A1 | 8/2011 | Menzel et al. | |
| 2011/0217783 A1 | 9/2011 | Caprioli et al. | |
| 2013/0062570 A1* | 3/2013 | Fukuyama | H01J 49/164 252/408.1 |
| 2013/0171349 A1 | 7/2013 | Takahashi et al. | |
| 2015/0276756 A1 | 10/2015 | Fukuyama et al. | |
| 2016/0011205 A1 | 1/2016 | Fukuyama et al. | |

FOREIGN PATENT DOCUMENTS

| | | |
|---|---|---|
| JP | 2013-217695 A | 10/2013 |
| JP | 2014-174015 A | 9/2014 |
| WO | 2014/136779 A1 | 9/2014 |

OTHER PUBLICATIONS

Fukuyama, Y., "MALDI Matrix Research for Biopolymers", The Mass Spectrometry Society of Japan, 2015, vol. 4, A0037, pp. 2-16E (15 pages).

Hudson Surface Technology, "µFocus Sample Plate for MALDI-TOF MS", 2010, pp. 2-17E (16 pages), https://www.sanyo-si.com/wp-content/uploads/15a7bbc2ba8d022ba681db1f58db75a3.pdf.

Yuko Fukuyama et al., "Alkylated Trihydroxyacetophenone as a MALDI Matrix for Hydrophobic Peptides," Analytical Chemistry; vol. 85 (2013) pp. 9444-9448.

Yuko Fukuyama et al., "Alkylated Dihydroxybenzoic Acid as a MALDI Matrix Additive for Hydrophobic Peptide Analysis," Analytical Chemistry; vol. 84 (2012) pp. 4237-4243.

Yuko Fukuyama et al., "Correction to Alkylated Dihydroxybenzoic Acid as a MALDI Matrix Additive for Hydrophobic Peptide Analysis," Analytical Chemistry; vol. 86 (2014) p. 5187.

Jeremy L. Norris et al., "Combination Detergent/MALDI Matrix: Functional Cleavable Detergents for Mass Spectrometry," Analytical Chemistry; vol. 77 (2005) pp. 5036-5040.

Michael Karas et al., "Matrix-assisted Laser Desorption/Ionization Mass Spectrometry with Additives to 2,5-Dihydroxybenzoic Acid," Organic Mass Spectrometry; vol. 28 (1993) pp. 1476-1481.

* cited by examiner

| | Hydrophobic peptide NF-kB Inhibitor (SSRCalc: 54.76) | Hydrophilic peptide Amyloid β 1-11 (SSRCalc: 13.47) |
|---|---|---|
| C8-ATHAP+4-CHCA (10+1) | | |
| C8-ATHAP | | ND |
| 4-CHCA | | |

```
                      SEQUENCE LISTING

<160> NUMBER OF SEQ ID NOS: 1

<210> SEQ ID NO 1
<211> LENGTH: 13
<212> TYPE: PRT
<213> ORGANISM: Human

<400> SEQUENCE: 1

Gly Pro His Arg Ser Thr Pro Glu Ser Arg Ala Ala Val
1               5                   10
```

MASS SPECTROMETRY METHOD USING MIXED MATRIX

BACKGROUND OF THE INVENTION

Technical Field of the Invention

The present invention relates to a mass spectrometry method that is applicable in medical and drug discovery fields, in particular, relates to a MALDI-MS (Matrix-Assisted Laser Desorption/Ionization Mass Spectrometry) application. More specifically, the present invention relates to a mass spectrometry method using a specific compound as a mixed matrix.

Background Art

Conditions for achieving efficient ionization of a molecule to be analyzed in the MALDI (Matrix-Assisted Laser Desorption/Ionization) mass spectrometry method have been researched. For example, JP-A-2005-326391 (Patent Document 1) discloses a method of ionizing a hydrophobic peptide with higher efficiency, as compared with the case of using α-cyano-4-hydroxycinnamic acid (4-CHCA) or 2,5-dihydroxybenzoic acid (DHB) which is a general matrix, by previously modifying a hydrophobic peptide with a 2-nitrobenzenesulphenyl group, and conducting a mass spectrometry using α-cyano-3-hydroxycinnamic acid (3-CHCA), 3-hydroxy-4-nitrobenzoic acid (3H4NBA), or a mixture of 3-CHCA and 3H4NBA as a matrix. In the MALDI mass spectrometry method disclosed in Patent Document 1, a certain extent of ionization promoting effect is obtained when modification of a molecule to be analyzed is performed, however, the ionization efficiency is not sufficient when such modification is not performed. Thus, there is a problem that the ionization efficiency in the MALDI mass spectrometry method is low for a molecular species for which MALDI ionization is difficult, in particular, such as a hydrophobic peptide.

3-CHCA

3H4NBA

For solving the above problem, WO2014/136779 (Patent Document 2) discloses a mass spectrometry method using a specific 2,4,6-trihydroxyalkylphenone (ATHAP) [alkylated trihydroxyacetophenone], for example, 1-(2,4,6-trihydroxyphenyl)octan-1-one, as a matrix. In the MALDI mass spectrometry method disclosed in Patent Document 2, it is possible to detect hydrophobic peptides with high sensitivity. In this analysis, ionization of hydrophilic peptides is suppressed, and it is difficult to analyze hydrophilic peptides. See also "Alkylated Trihydroxyacetophenone as a MALDI Matrix for Hydrophobic Peptides", by Yuko Fukuyama et al., Anal. Chem. 2013, 85, 9444-9448 (Non-Patent Document 1).

Example of ATHAP:
1-(2,4,6-trihydroxyphenyl)octan-1-one

JP-A-2013-190250 (Patent Document 3) and US 2015/0276756 (Patent Document 4) disclose a mass spectrometry method using a general matrix such as α-cyano-4-hydroxycinnamic acid (4-CHCA), 2,5-dihydroxybenzoic acid (DHB) or the like, and 2,5- or 3,5-dihydroxybenzoic acid ester (alkylated dihydroxybenzoic acid; ADHB, e.g., octyl 2,5-dihydroxybenzoate) as a matrix additive. In the MALDI mass spectrometric method disclosed in Patent Documents 3 and 4, it is possible to detect hydrophobic peptides with high sensitivity. At the time of a mass spectrometry, a hydrophobic peptide is concentrated in an outer edge part of a sample/matrix mixed crystal on a mass spectrometry plate. See also "Alkylated Dihydroxybenzoic Acid as a MALDI Matrix Additive for Hydrophobic Peptide Analysis", by Yuko Fukushima et al., Anal. Chem. 2012, 84, 4237-4243 (Non-Patent Document 2); and a corrected version of Non-Patent Document 2, Anal. Chem. 2014, 86, 5187-5187 (Non-Patent Document 3).

Example of ADHB: octyl 2,5-dihydroxybenzoate

4-CHCA

US 2011/0217783 (Patent Document 5) and US 2006/0240562 (Patent Document 6) disclose 2-cyano-3-[4-[(dodecyloxy)methoxy]phenyl]acrylic acid (1) obtained by introducing an alkyloxymethyl group to a hydroxyl group of α-cyano-4-hydroxycinnamic acid (4-CHCA) which is a general matrix, and 3-(4-dodecyloxymethyloxy-3,5-dimethyloxyphenyl)acrylic acid (2) obtained by introducing an alkyloxymethyl group to a hydroxyl group of sinapic acid (SA) which is a general matrix; and disclose a mass spectrometry method using the compound (1) or (2) wherein the compound (1) or (2) functions as a solvent (surface active agent) for poorly-soluble protein, and then functions as a matrix as a result of cleavage of the alkyl chain moiety from the linker part under acidic conditions, and improves the sensitivity to hydrophobic peptides through a series of process. See also Anal. Chem. 2005, 77, 5036-5040 (Non-Patent Document 4).

JP-A-2013-134102 (Patent Document 10) discloses a mass spectrometry method in which the ionization efficiency of hydrophobic peptides is improved by using an alkyl alcohol having 4 to 14 carbon atoms as a matrix additive.

US 2009/0269855 (Patent Document 7) discloses a mass spectrometry method of improving an S/N ratio of dynorphin which is a hydrophobic peptide by using 2-hydroxy-5-octyloxybenzoic acid as a matrix.

JP-A-2013-164382 (Patent Document 8) discloses a mass spectrometry method in which the ionization efficiency of hydrophobic peptides is improved by using a cinnamic acid derivative having the following structure as a matrix additive. In the formula, R represents an alkyl group having 4 to 16 carbon atoms, and the —OR group and the —CH═C(CN)COOH group are substituted mutually at a meta position or a para position.

JP-A-2013-217695 (Patent Document 9) discloses a mass spectrometry method in which the ionization efficiency of hydrophobic peptides is improved by using an amide of p-nitroaniline having the following structure as a matrix additive. In the formula, R represents an alkyl group having 4 to 14 carbon atoms.

JP-A-2014-174015 (Patent Document 11) discloses a mass spectrometry method in which the ionization efficiency of hydrophobic peptides is improved by using a dialkoxybenzoic acid derivative (I) or (II) having the following structure as a matrix additive. In formula (3), Me represents a methyl group, and $R^{11}$ and $R^{12}$, which may be the same or different, each represent an alkyl group having 2 to 8 carbon atoms. In formula (4), R represents a hydrogen atom or a methyl group, and $R^{21}$ and $R^{22}$, which may be the same or different, each represent an alkyl group having 2 to 8 carbon atoms.

US 2011/0207227 (Patent Document 12) discloses a mass spectrometry method including: previously forming a microcrystalline spot of matrix on a MALDI sample plate having a hydrophobic region, applying a sample on the microcrystalline spot of matrix, washing the sample on the microcrystalline spot of matrix, and analyzing the sample by MS measurement.

Org. Mass Spectrom. 28, 1476-1481, 1993 (Non-Patent Document 5) discloses a mixed matrix super-DHB of 2,5-dihydroxybenzoic acid (DHB) and 5-methyoxysalicylic acid. In this mixed matrix, the sensitivity to proteins and sugar chains is improved, relative to DHB.

CITATION LIST

Patent Documents

Patent Document 1: JP-A-2005-326391
Patent Document 2: WO 2014/136779
Patent Document 3: JP-A-2013-190250
Patent Document 4: US 2015/0276756
Patent Document 5: US 2011/0217783
Patent Document 6: US 2006/0240562
Patent Document 7: US 2009/0269855
Patent Document 8: JP-A-2013-164382
Patent Document 9: JP-A-2013-217695
Patent Document 10: JP-A-2013-134102
Patent Document 11: JP-A-2014-174015
Patent Document 12: US 2011/0207227

Non-Patent Documents

Non-Patent Document 1: Anal. Chem. 2013, 85, 9444-9448
Non-Patent Document 2: Anal. Chem. 2012, 84, 4237-4243
Non-Patent Document 3: Anal. Chem. 2014, 86, 5187-5187
Non-Patent Document 4: Anal. Chem. 2005, 77, 5036-5040
Non-Patent Document 5: Org. Mass Spectrom. 1993, 28, 1476-1481

SUMMARY OF THE INVENTION

Problems to be Solved by the Invention

As described above, in the MALDI mass spectrometry method, various investigations have been made for improving the sensitivity to hydrophobic peptides that is poor when a general matrix such as α-cyano-4-hydroxycinnamic acid (4-CHCA) or 2,5-dihydroxybenzoic acid (DHB) is used. Although use of 2,4,6-trihydroxyalkylphenone (ATHAP) as a matrix as described in Patent Document 2 enables detection of hydrophobic peptides with high sensitivity, it is difficult to analyze hydrophilic peptides because ionization of hydrophilic peptides is suppressed.

Thus, a matrix capable of analyzing peptides having a wide range of degrees of hydrophobicity (from hydrophilic to hydrophobic) has not been found yet at present.

For example, as disclosed in Patent Document 3, a hydrophobic peptide may be concentrated in an outer edge part of a sample/matrix mixed crystal on the mass spectrometry plate at the time of a mass spectrometry. In such a case, laser irradiation on the outer edge part of the mixed crystal at the time of a mass spectrometry of the mixture sample causes ionization of hydrophobic peptides, and enables analysis of the hydrophobic peptides with excellent sensitivity. However, in the case where a hydrophobic peptide is not concentrated in the outer edge part of the sample/matrix mixed crystal, a plurality of substances in the sample exist in the same site of the laser irradiation, and ionization of any of the substances is suppressed, and thus the sensitivity of the any of the substances can deteriorate.

Also when a general matrix (e.g., DHB) is used, there is a problem that the sweet spot deviates and the analysis requires a long time.

It is an object of the present invention to provide a mass spectrometry method using a mixed matrix, capable of easily and efficiently improving the ionization efficiency in mass spectrometry for peptides having a wide range of degrees of hydrophobicity (from hydrophilic to hydrophobic).

Means for Solving the Problems

As a result of diligent effort, the present inventors found that use of a mixed matrix of a specific 2,4,6-trihydroxyalkylphenone [alkylated trihydroxyacetophenone], and a general matrix such as α-cyano-4-hydroxycinnamic acid (4-CHCA), 2,5-dihydroxybenzoic acid (DHB), 2,4,6-trihydroxyacetophenone (THAP) or the like enables efficient ionization of even a molecular species such as a hydrophobic compound for which ionization is difficult, and also enables ionization of a molecular species that is more hydrophilic than the hydrophobic compound, and accomplished the present invention.

The present invention includes the followings.

(1) A MALDI mass spectrometry method for analyzing a sample using as a mixed matrix, 2,4,6-trihydroxyalkylphenone represented by the following general formula (I):

wherein R represents an alkyl group having 3 to 12 carbon atoms, and a matrix (II) for mass spectrometry that is more hydrophilic than 2,4,6-trihydroxyalkylphenone represented by the formula (I) wherein R is an alkyl group having 3 carbon atoms.

(2) The mass spectrometry method according to the above (1), wherein the compound represented by the general formula (I) is 1-(2,4,6-trihydroxyphenyl)octan-1-one having the following structure:

(3) The mass spectrometry method according to the above (1) or (2), wherein the matrix (II) for mass spectrometry is selected from the group consisting of α-cyano-4-hydroxycinnamic acid (4-CHCA), 2,5-dihydroxybenzoic acid (DHB), and 2,4,6-trihydroxyacetophenone (THAP).

(4) The mass spectrometry method according to any one of the above (1) to (3), wherein a hydrophobic focus plate is used.

(5) The mass spectrometry method according to any one of the above (1) to (4), wherein a sample to be analyzed is a mixture sample containing a peptide and a compound other than peptide.

(6) The mass spectrometry method according to any one of the above (1) to (5), wherein the sample to be analyzed is a mixture sample containing a plurality of peptides having different hydrophobicity. The term peptide includes protein.

(7) The mass spectrometry method according to any one of the above (1) to (6), wherein the sample to be analyzed is a mixture sample containing a protein digest.

In particular, the mass spectrometry method according to any one of the above (1) to (6), wherein the sample to be analyzed is a mixture sample containing a membrane protein digest.

Advantageous Effect of the Invention

In the present invention, 2,4,6-trihydroxyalkylphenone having an alkyl group having 3 to 12 carbon atoms (namely, R in general formula (I)), and a general matrix (II) for mass spectrometry that is more hydrophilic than 2,4,6-trihydroxyalkylphenone represented by the general formula (I) (wherein, R is an alkyl group having 3 carbon atoms) are used in combination as matrixes for mass spectrometry. When 2,4,6-trihydroxyalkylphenone having an alkyl group R having 3 to 12 carbon atoms is used as a matrix for mass spectrometry, it is possible to improve the ionization efficiency of molecular species for which ionization is difficult such as hydrophobic compounds, in particular, hydrophobic peptides. And by using the general matrix (II) for mass spectrometry that is more hydrophilic in combination, not only hydrophobic peptides but also more hydrophilic molecular species can be ionized. Therefore, according to the present invention, it is possible to ionize and analyze peptides and compounds other than peptide having a wide range of degrees of hydrophobicity (from hydrophilic to hydrophobic) easily and efficiently. Thus, according to the present invention, the detection sensitivity is improved by the mass spectrometry measurement of peptides having a wide range of degrees of hydrophobicity (from hydrophilic to hydrophobic), and coverage of various samples is improved.

Also, in the present invention, when a hydrophobic focus plate is used, ion detection sites of hydrophilic peptides and hydrophobic peptides are separated from each other on the plate. This makes it possible to specify the laser irradiation site depending on the hydrophobicity degree of the compound contained in the sample to be analyzed, and enables rapid analysis.

BRIEF DESCRIPTION OF THE DRAWINGS

FIG. 11(c) shows a mass spectrum result of the peptide mixture containing fourteen kinds of peptides when 4-CHCA is used as a single matrix in Comparative Example 1. The horizontal axis indicates a mass/charge (m/z), the vertical axis indicates a relative intensity of ion (% Int.). Each chart shows a mass range of m/z: 3000 to 5000.

MODES FOR CARRYING OUT OF THE INVENTION

[Matrix]

The present invention provides a MALDI mass spectrometry method for analyzing a sample using as a mixed matrix 2,4,6-trihydroxyalkylphenone represented by the following general formula (I), and a matrix for mass spectrometry (II) that is more hydrophilic than 2,4,6-trihydroxyalkylphenone wherein R is an alkyl group having 3 carbon atoms represented by the formula (I).

In the general formula (I), R represents an alkyl group having 3 to 12 carbon atoms, for example, 3 to 11 carbon atoms. That is, the number of carbon atoms in the acyl group (—CO—R) including the carbonyl group is 4 to 13, for example, 4 to 12. In the present specification, a compound represented by the general formula (I) (R is an alkyl group having 3 to 12 carbon atoms) is also written as ATHAP (alkylated trihydroxyalkylphenone). For example, when the number of carbon atoms in the acyl group (—CO—R) including the carbonyl group is 8 (that is, the alkyl group R is a heptyl group), the compound is written as C8-ATHAP. The compound 2,4,6-trihydroxyacetophenone (R is a $CH_3$ group), that is out of the range of the general formula (I), is written as THAP.

Examples of the alkyl group having 3 to 12 carbon atoms represented by R in the general formula (I) include a propyl group, a butyl group, a pentyl group, a hexyl group, a heptyl group, an octyl group, a nonyl group, a decyl group, an undecyl group, and a dodecyl group. These alkyl groups may be of a straight chain or branched. Examples of a branched alkyl group include an isopropyl group, an isobutyl group, a sec-butyl group, and a 2-ethylhexyl group. Among these, an alkyl group having 5 to 11 carbon atoms is preferred, an alkyl group having 5 to 9 carbon atoms is more preferred, and an alkyl group having 7 carbon atoms (as the acyl group including the carbonyl group, an octan-1-one group having 8 carbon atoms; namely, C8-ATHAP) is particularly preferred. When the analyte is a hydrophobic compound, it is considered that the alkyl group represented by R requires having a certain degree of hydrophobicity for ionization of the hydrophobic compound.

C8-ATHAP

When 2,4,6-trihydroxyalkylphenone having an alkyl group having 3 to 12, for example, 3 to 11 carbon atoms is used as a matrix for mass spectrometry, it is possible to improve the ionization efficiency of molecular species for which ionization is difficult such as hydrophobic compounds, in particular, hydrophobic peptides.

In the present invention, the matrix ATHAP (R=C3-12) of the general formula (I), and the matrix (II) for mass spectrometry that is more hydrophilic than the compound having a C3 alkyl group as R, said compound having the lowest hydrophobicity among compounds represented by the formula (I) are used as amixedmatrix. By using the more hydrophilic matrix (II) for mass spectrometry, not only hydrophobic peptides but also more hydrophilic molecular species can be ionized. Therefore, it is possible to easily and efficiently ionize and analyze peptides and compounds other than peptide having a wide range of degrees of hydrophobicity (from hydrophilic to hydrophobic). Thus, the detection sensitivity by the mass spectrometric measurement of peptides having a wide range of degrees of hydrophobicity (from hydrophilic to hydrophobic) is improved, and coverage of various samples is improved.

The matrix (II) for mass spectrometry may be appropriately selected from known matrixes. For example, α-cyano-4-hydroxycinnamic acid (4-CHCA), 2,5-dihydroxybenzoic acid (DHB), and 2,4,6-trihydroxyacetophenone (THAP) may be recited.

In the present invention, the concentration of the matrix solution containing the matrix ATHAP represented by the general formula (I) and the matrix (II) may be selected, for example, as follows. The solution concentration of the matrix ATHAP represented by the general formula (I) may be, for example, about 0.01 mg/mL to 10 mg/mL (saturated concentration), preferably about 0.05 mg/mL to 5 mg/mL, more preferably about 0.05 mg/mL to 1 mg/mL. The solution concentration of the matrix (II) may be, for example, about 0.01 mg/mL to 10 mg/mL (saturated concentration), preferably about 0.05 mg/mL to 5 mg/mL, more preferably about 0.05 mg/mL to 1 mg/mL.

In the present invention, the mixing ratio of the matrix ATHAP (I) and the matrix (II) in the matrix solution prepared to have the above concentration is not particularly limited depending on the object to be measured, and for example, the mixing ratio may be, for example, about 50:1 to 1:10, preferably about 10:1 to 1:10, more preferably about 10:1 expressed by the volume ratio [(I):(II)] between the solution of the matrix ATHAP represented by the general formula (I) and the solution of the matrix (II).

[Analyte for Mass Spectrometry]

An analyte for mass spectrometry using the mixed matrix in the present invention is not particularly limited. For example, the analyte may be a molecule (including peptide, and a molecule other than peptide) having a molecular weight of 500 to 30,000, preferably 1,000 to 10,000. Preferably, the matrix of the present invention is suitably used for mass spectrometry of a mixture of a hydrophobic substance and a hydrophilic substance because the matrix can promote ionization of both of the hydrophobic substance and the hydrophilic substance. In other words, the sample may contain other substance (for example, hydrophilic substance) in addition to the hydrophobic substance which is an analyte.

As demonstrated in Examples, the mixed matrix of the present invention can promote ionization of a hydrophobic substance compared with the case where α-cyano-4-hydroxycinnamic acid (4-CHCA) which is a conventional matrix is used solely. Also, it is possible to promote ionization of a hydrophilic substance compared with the case where ATHAP is used solely. Therefore, even when the sample contains both a hydrophobic substance and a hydrophilic substance, both the hydrophobic substance and the hydrophilic substance can be easily analyzed. From this point, the matrix of the present invention can be suitably applied to mass spectrometry of a mixture of a hydrophobic substance and a hydrophilic substance. Even when the sample contains either one of a hydrophobic substance or a hydrophilic substance, the one can be easily analyzed.

The degree of hydrophobicity is not particularly limited, and may be such a degree that the substance can be determined as hydrophobic on the basis of various known indexes of hydrophobicity or methods for calculating degree of hydrophobicity. For example, the degree of hydrophobicity of a hydrophobic substance may be such a degree that a person skilled in the art can determine that the substance is hydrophobic according to BB index (Bull and Breese Index). More specifically, BB index of the hydrophobic substance may be, for example, not more than 1,000, preferably not more than −1,000. In this case, the degree of hydrophilicity of a hydrophilic substance may be a value of, for example, more than 1,000, preferably, more than 2,000.

Alternatively, the degree of hydrophobicity of a hydrophobic substance may be such a degree that a person skilled in the art can determine that the substance is hydrophobic according to HPLC index. The HPLC index is a hydrophobicity index based on the reverse phase HPLC retention time using an acetonitrile aqueous solution containing 0.13% heptafluoro-n-butyric acid (HFBA) as an eluate, reported in Analytical Biochemistry, 124, 201-208, 1982 by C. A. Browne, H. P. J. Bennett, and S. Solomon, and is also called "HPLC/HFBA retention". More specifically, HPLC index of the hydrophobic substance may be, for example, not less than 40, for example, 40 to 10,000, preferably 100 to 1,000. In this case, the degree of hydrophilicity of a hydrophilic substance may be a value of, for example, less than 40, preferably, less than 20.

Further, the degree of hydrophobicity of a hydrophobic substance in the present invention may be such a degree that a person skilled in the art can determine that the substance is hydrophobic according to SSRCalc Hydrophobicity. The SSRCalc Hydrophobicity is reported in Analytical Biochemistry, 78, 7785-7795, 2006 by Oleg V. Krokhin. The SSRCalc Hydrophobicity is a hydrophobicity index based on a peptide sequence-specific algorism, sequence-specific retention calculator (SSRCalc) for the retention time of RP-HPLC (reverse phase high performance liquid chromatography) of peptide. While the HPLC index or the BB index estimates the retention time on the basis of only amino acid composition information, the SSRCalc Hydrophobicity estimates the retention time on the basis of information including the primary structure and the secondary structure of the peptide. In the present invention, when the analyte is a hydrophobic peptide, the SSRCalc Hydrophobicity is suitably used as an index for the degree of hydrophobicity. More specifically, SSRCalc Hydrophobicity (by the Manitoba Centre for Proteomics and Systems Biology, available at http://hs2.proteome.ca/SSRCalc/SSRCalcX.html) of the hydrophobic substance may be, for example, not less than 30, preferably 40 to 70. In this case, the degree of hydrophilicity of the hydrophilic substance may be a value of, for example, less than 30, preferably less than 25. In the present invention, it is possible to analyze a mixture sample of substances having a wide range of degrees of hydrophobicity (from hydrophilic to hydrophobic), for example, having a SSRCalc Hydrophobicity of about 0 to 90.

In the present invention, owing to the matrix ATHAP (I), the effect of enhancing the ability to ionize hydrophobic peptides (peptide includes protein, in the present invention) is particularly high. Whether or not the peptide is hydrophobic can be determined according to BB index, HPLC index, or SSRCalc Hydrophobicity, preferably SSRCalc Hydrophobicity as an index, and concretely, the peptide may be composed of more amino acids having higher hydrophilicity. Examples of hydrophilic amino acid include isoleucine, leucine, valine, alanine, phenylalanine, proline, methionine, tryptophan, and glycine. Cysteine, tyrosine and the like may be contained. Hydrophobic peptides do not depend merely on such a primary structure of peptide, but may have a higher structure having higher hydrophobicity. For example, as a hydrophobic peptide, a peptide having a structure that is easy to interact with the hydrophobic stationary phase surface used in the reverse phase HPLC column can be recited. Further, by using the more hydrophilic matrix (II) for mass spectrometry, not only hydrophobic peptides but also more hydrophilic molecular species can be ionized.

[Preparation of Crystal for Mass Spectrometry]

A crystal for mass spectrometry can be obtained through the step of forming, on a target plate for mass spectrometry, a liquid droplet of a mixture liquid containing at least an analyte and a matrix in a solvent, and the step of removing the solvent from the formed liquid droplet of the mixture liquid to obtain a non-volatile matter (i.e., at least the analyte and the matrix) contained in the mixture liquid as a residue. The obtained residue is a crystal for mass spectrometry. In this specification, the term "crystal for mass spectrometry" is synonymous with the term "residue".

As the target for mass spectrometry, a conductive metal plate usually used in MALDI mass spectrometry may be used. Specifically, a plate made of stainless steel or gold may be used. By using a hydrophobic focus plate, it is possible to concentrate hydrophobic substances in the focus part of the plate.

A specific method for preparing the liquid droplet of the mixture liquid on the target plate is not particularly limited. For example, first, a sample solution containing an analyte, and a matrix solution are prepared separately from each other. Then, these solutions are mixed to obtain a mixture liquid, and the obtained mixture liquid is dropped onto a target plate. Alternatively, these solutions may be mixed on a target plate by dropping these solutions onto the same position on the target plate (on-target mix method). In the case of on-target mix method, the order of dropping the solutions is not particularly limited.

The solvent of the mixture liquid may be selected from the group consisting of acetonitrile (ACN), trifluoroacetic acid (TFA), methanol (MeOH), ethanol (EtOH), tetrahydrofuran (THF), dimethyl sulfoxide (DMSO), water, and the like. More specifically, as the solvent of the mixture liquid, for example, an aqueous ACN-TFA solution, an aqueous ACN solution, an aqueous MeOH-TFA solution, an aqueous MeOH solution, an aqueous EtOH-TFA solution, an aqueous EtOH solution, an aqueous THF-TFA solution, an aqueous THF solution, an aqueous DMSO-TFA solution, an aqueous DMSO solution or the like is used, and more preferably, an aqueous ACN-TFA solution or an aqueous ACN solution may be used. The concentration of ACN in the aqueous ACN-TFA solution may be, for example, 10 vol % to 90 vol %, preferably 25 vol % to 75 vol %, and the concentration of TFA in the aqueous ACN-TFA solution may be, for example, 0.05 vol % to 1 vol %, preferably 0.05 vol % to 0.1 vol %.

The volume of the liquid droplet of the mixture liquid is not particularly limited, and may be appropriately determined by those skilled in the art. When a well is provided on the target plate, the liquid droplet of the mixture liquid may be formed in the well. In this case, the liquid droplet is formed so as to have a volume that can be held in the well. More specifically, the liquid droplet may be formed so as to have a volume of about 0.1 μL to 2 μL, for example, about 0.5 μL.

Next, the solvent is removed from the liquid droplet of the mixture liquid on the target plate. The removal of the solvent includes natural evaporation of the solvent. The amount of the matrix contained per one residue (that is, per one crystal for mass spectrometry) generated by evaporation may be, for example, 1 pmol to 1,000 nmol, preferably 10 pmol to 100 nmol as a guide. The amount of the analyte may be in the range of, for example, 1 amol to 100 pmol, or in the range of 100 amol to 50 pmol of sample with respect to 10 nmol of the matrix.

The residue has a substantially circular shape on a surface in contact with the target plate. That is, the outer edge of the residue is substantially circular. The average diameter of the substantially circular shape may vary depending on the amount of the sample, the volume of the liquid droplet, the amount of the matrix, the composition of the solvent etc., but is for example 0.1 mm to 3 mm, preferably 0.5 mm to 2 mm. It is to be noted that the average diameter is the average of the lengths of line segments cut from lines passing through the center of gravity of the substantially circular shape by the outer edge of the residue in one residue.

When an ordinary metallic plate is used as the target for mass spectrometry, the substance to be analyzed mainly exists in the substantial circle in the substantially circular residue obtained by removal of the solvent. Therefore, it is possible to easily ionize the substance to be analyzed without specifying the laser irradiation position at the time of ionization. On the other hand, when a hydrophobic focus plate is used as a target for mass spectrometry, a hydrophobic substance is easy to concentrate in the focus part of the plate, so that the hydrophobic substance becomes easy to be detected by laser radiation to the focus part.

[Mass Spectrometer]

A mass spectrometer used in the present invention is not particularly limited insofar as the mass spectrometer is combined with a MALDI (Matrix-Assisted Laser Desorption/Ionization) ion source. Examples of such a mass spectrometer include a MALDI-TOF (Matrix-Assisted Laser Desorption/Ionization-Time-of-Flight) mass spectrometer, a MALDI-IT (Matrix-Assisted Laser Desorption/Ionization-Ion Trap) mass spectrometer, a MALDI-IT-TOF (Matrix-Assisted Laser Desorption/Ionization-Ion Trap-Time-of-Flight) mass spectrometer, and a MALDI-FTICR (Matrix-Assisted Laser Desorption/Ionization-Fourier Transformation Ion Cyclotron Resonance) mass spectrometer.

EXAMPLES

Hereinbelow, the present invention will be described specifically with reference to examples, but is not limited to the following examples.

Example 1

In Example 1, C8-ATHAP (1-(2,4,6-trihydroxyphenyl) octane-1-one), and 4-CHCA (α-cyano-4-hydroxycinnamic acid) were used as a mixed matrix.

As fourteen kinds of peptides having different degrees of hydrophobicity, following peptides were used.

No. 1: NF-kB Inhibitor (SSRCalc Hydrophobicity: 54.76),
No. 2: Melittin (SSRCalc Hydrophobicity: 53.82),
No. 3: Amyloid β 1-42 (SSRCalc Hydrophobicity: 51.06),
No. 4: OVA-BIP hybrid peptide (SSRCalc Hydrophobicity: 50.23),
No. 5: Humanin (SSRCalc Hydrophobicity: 49.95),
No. 6: [Gly14]-Humanin (SSRCalc Hydrophobicity: 49.51),
No. 7: Temporin A, amide (SSRCalc Hydrophobicity: 45.59),
No. 8: MPGANLS (SSRCalc Hydrophobicity: 45.15),
No. 9: Amyloid β 22-42 (SSRCalc Hydrophobicity: 42.37),
No. 10: ACTH 18-39 (SSRCalc Hydrophobicity: 37.86),
No. 11: Amyloid β-28 (SSRCalc Hydrophobicity: 36.31),
No. 12: Amyloid β-11 (SSRCalc Hydrophobicity: 13.47),
No. 13: GPHRSTPESRAAV (SSRCalc Hydrophobicity: 10.58) (SEQ ID NO: 1), and
No. 14: β-conglycinin 165-178 (SSRCalc Hydrophobicity: 7.19).

(1) As a sample solution, a 0.02 fmol/μL to 20 fmol/μL peptide mixture containing the above fourteen kinds of peptides (SSRCalc Hydrophobicity: 7.19 to 54.76) in 50% ACN water was prepared.

(2) As a matrix solution, 0.1 mg/mL C8-ATHAP in 75% ACN, 0.1% TFA water was prepared, and 0.1 mg/mL 4-CHCA in 75% ACN, 0.1% TFA water was prepared.

(3) As a desalting additive, methylenediphosphonic acid (MDPNA) was prepared as 0.02% MDPNA in water, or as 0.02% MDPNA in 75% ACN, 0.1% TFA water.

(4) As a mixed matrix solution, the C8-ATHAP solution and the 4-CHCA solution of (2) were mixed at 10:1 (v/v), and to the resultant solution, an equivalent amount of either one of the 0.02% MDPNA solutions of (3) was added, to prepare respective C8-ATHAP+4-CHCA (10+1) solutions.

(5) On a hydrophobic μFocus 600 m MALDI plate (Hudson Surface Technology Inc., NJ, USA), 0.5 μL of the sample solution of (1) was dropped, and then 0.5 μL of the mixed matrix solution of (4) was dropped (on-target mix method).

(6) After the solvent was volatilized, measurement was conducted by raster analysis in the positive ion mode and linear mode of the MALDI TOFMS [AXIMA Performance (registered tradename), Shimadzu/Kratos, UK].

Comparative Example 1

In Comparative Example 1, C8-ATHAP (1-(2,4,6-trihydroxyphenyl)octan-1-one), or 4-CHCA (α-cyano-4-hydroxycinnamic acid) that is the same as that used in Example 1 was used as a single matrix.

As fourteen kinds of peptides having different degrees of hydrophobicity, those the same as those used in Example 1 were used.

(1) As a sample solution, a 0.02 fmol/μL to 20 fmol/μL peptide mixture containing the above fourteen kinds of peptides (SSRCalc Hydrophobicity: 7.19 to 54.76) in 50% ACN water was prepared.

(2) As a matrix solution, 0.1 mg/mL C8-ATHAP in 75% ACN, 0.1% TFA water was prepared, and 0.1 mg/mL 4-CHCA in 75% ACN, 0.1% TFA water was prepared.

(3) As a desalting additive, methylenediphosphonic acid (MDPNA) was prepared as 0.02% MDPNA in water, or as 0.02% MDPNA in 75% ACN, 0.1% TFA water.

(4) As a single matrix solution, to the C8-ATHAP solution of (2), an equivalent amount of either one of the 0.02% MDPNA solutions of (3) was added to prepare respective C8-ATHAP single matrix solutions.

Similarly, to the 4-CHCA solution of (2), an equivalent amount of either one of the 0.02% MDPNA solutions of (3) was added to prepare respective 4-CHCA single matrix solutions.

(5) On a hydrophobic μFocus 600 μm MALDI plate (Hudson Surface Technology Inc., NJ, USA), 0.5 μL of the sample solution of (1) was dropped, and then 0.5 μL of the C8-ATHAP single matrix solution of (4) was dropped (on-target mix method). Similarly, on a hydrophobic μFocus 600 μm MALDI plate (Hudson Surface Technology Inc., NJ, USA), 0.5 μL of the sample solution of (1) was dropped, and then 0.5 μL of the 4-CHCA single matrix solution of (4) was dropped (on-target mix method).

(6) After the solvent was volatilized, measurement was conducted by raster analysis in the positive ion mode and linear mode of the MALDI TOFMS [AXIMA Performance (registered tradename), Shimadzu/Kratos, UK].

Figure 2A:
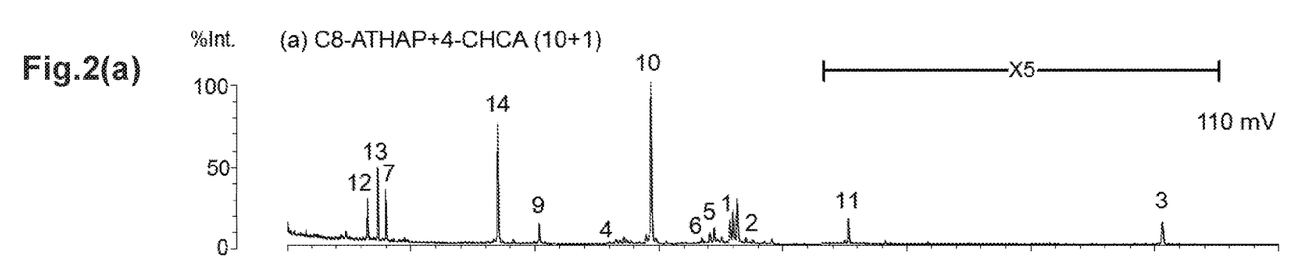
FIGS. 2(a), (b) and (c) show the mass spectrum results of the same measurements as in FIGS. 1(a), (b) and (c), respectively, but FIGS. 2(a), (b) and (c) show a mass range of m/z: 1000 to 5000.
Figure 2B:
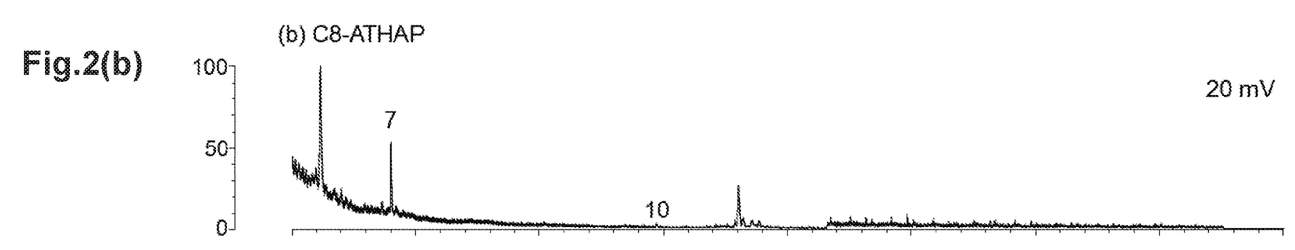
Figure 2C:
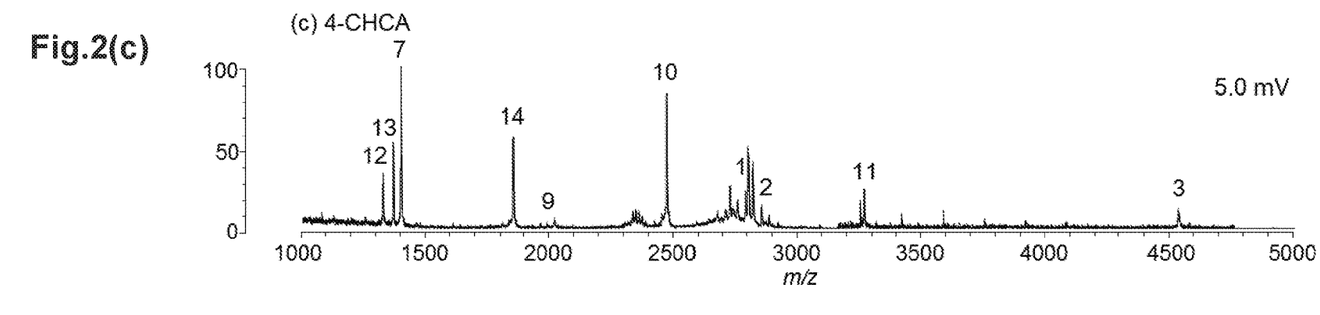
Figure 3:
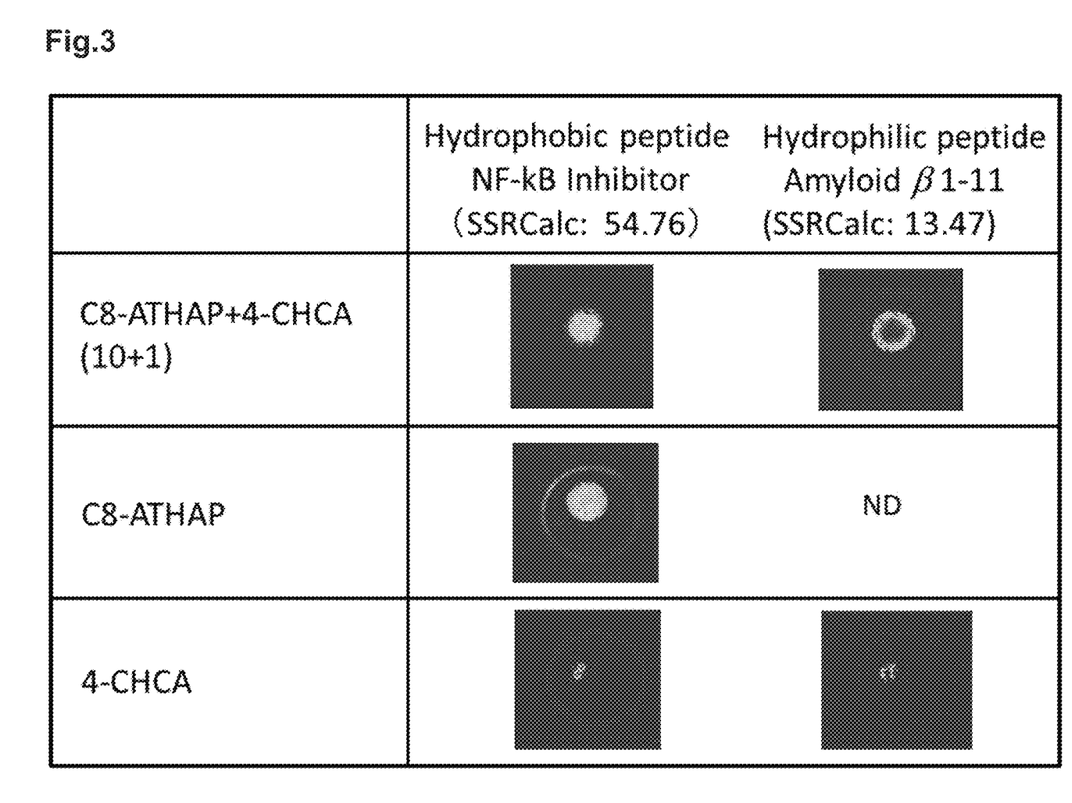
FIG. 3 shows images of mass imaging of hydrophobic peptide NF-kB Inhibitor and hydrophilic peptide Amyloid β 1-11 in wells on the MALDI plate in Example 1 and Comparative Example 1.

The obtained results are shown in FIGS. 1 to 3, and Table 1.

Figure 1A:
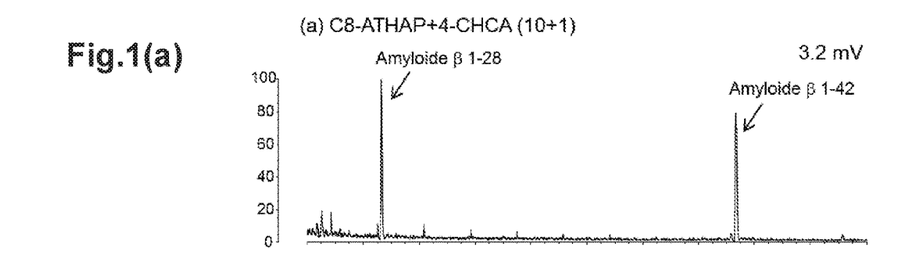
FIG. 1(a) shows a mass spectrum result of a peptide mixture containing fourteen kinds of peptides having different degrees of hydrophobicity when C8-ATHAP and 4-CHCA are used as a mixed matrix in Example 1.
Figure 1B:
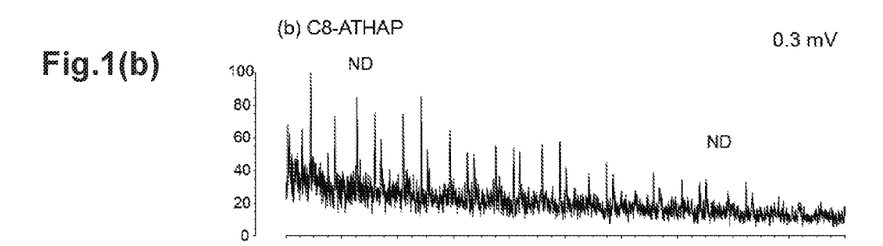
FIG. 1(b) shows a mass spectrum result of the peptide mixture containing fourteen kinds of peptides when C8-ATHAP is used as a single matrix in Comparative Example 1.
Figure 1C:
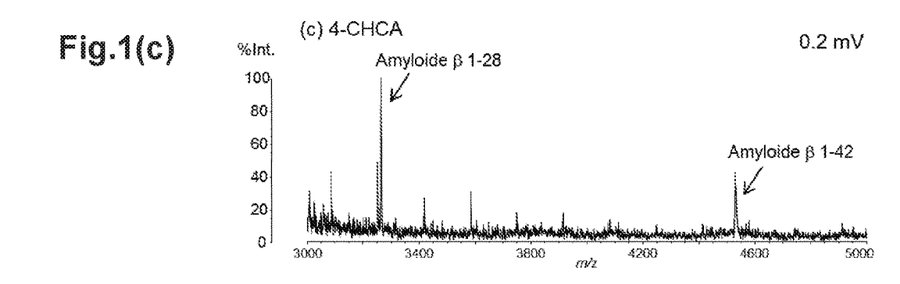

FIG. 1(*a*) shows a mass spectrum result of when C8-ATHAP and 4-CHCA are used as a mixed matrix in Example 1 (1 fmol/well). FIG. 1(*b*) shows a mass spectrum result when C8-ATHAP is used as a single matrix in Comparative Example 1 (1 fmol/well). FIG. 1(*c*) shows a mass spectrum result when 4-CHCA is used as a single matrix in Comparative Example 1 (1 fmol/well). In any of these charts, the part in the mass range of m/z: 3,000 to 5,000 is shown. FIGS. 2(*a*), (*b*) and (*c*) show the mass spectrum results of the same measurements as those in FIGS. 1(*a*), (*b*) and (*c*), respectively, but FIGS. 2(*a*), (*b*) and (*c*) show the mass range of m/z: 1,000 to 5,000.

According to FIG. 1, when C8-ATHAP was used as a single matrix, neither hydrophilic peptide: Amyloid β 1-28 (SSRCalc Hydrophobicity: 36.31), nor hydrophobic peptide: Amyloid β 1-42 (SSRCalc Hydrophobicity: 51.06) was detected at the sample concentration of 1 fmol/well [FIG. 1(*b*)]. When 4-CHCA was used as a single matrix, both Amyloid β 1-28 and Amyloid β 1-42 were detected, however, the S/N was low, and the detection sensitivity of hydrophobic peptide: Amyloid β 1-42 was low [FIG. 1(*c*)]. When C8-ATHAP and 4-CHCA were used as a mixed matrix, both Amyloid β 1-28 and Amyloid β 1-42 were detected with high S/N and high sensitivity [FIG. 1(*a*)].

FIGS. 2(*a*), (*b*) and (*c*) reveal that when C8-ATHAP and 4-CHCA were used as a mixed matrix, the fourteen kinds of peptides ranging from hydrophilic to hydrophobic were detected in a wide mass range with high S/N and high sensitivity. The "No." upper each peak in FIGS. 2(*a*), (*b*) and (*c*) corresponds to peptide No. of the fourteen kinds of peptides, and indicates the peak derived from each peptide.

TABLE 1

| | | | Detection Limit | | | | | |
|---|---|---|---|---|---|---|---|---|
| | | | C8-ATHAP | | C8-ATHAP + 4-CHCA (10 + 1) | | 4-CHCA | |
| No. | SSRCalc | m/z | MDPNA (/water) | MDPNA (/75% ACN, 0.1% TFAwater) | MDPNA (/water) | MDPNA (/75% ACN, 0.1% TFAwater) | MDPNA (/water) | MDPNA (/75% ACN, 0.1% TFAwater) |
| 1 | 54.76 | 2781.5 | 10 | 10 | 1 | 0.1 | 1 | 1 |
| 2 | 53.82 | 2846.5 | 10 | 10 | 1 | 1 | 1 | 1 |
| 3 | 51.06 | 4512.3 | 10 | 10 | 1 | 1 | ND | 10 |
| 4 | 50.23 | 2290.5 | 10 | 10 | 1 | 1 | ND | ND |
| 5 | 49.95 | 2687.2 | 10 | 10 | 1 | 1 | ND | ND |
| 6 | 49.51 | 2657.2 | 10 | 10 | 1 | 1 | ND | ND |
| 7 | 45.59 | 1396.8 | 10 | 1 | 1 | 0.1 | 0.1 | 1 |
| 8 | 45.15 | 2766.2 | 10 | ND | 10 | 10 | ND | ND |
| 9 | 42.37 | 1999.3 | 10 | 10 | 1 | 0.1 | 1 | 1 |
| 10 | 37.86 | 2465.7 | 1 | 1 | 0.1 | 0.1 | 0.1 | 0.1 |
| 11 | 36.31 | 3261.5 | ND | ND | 1 | 1 | 1 | 1 |
| 12 | 13.47 | 1325.3 | ND | ND | 1 | 0.1 | 1 | 1 |
| 13 | 10.58 | 1364.5 | 10 | ND | 1 | 0.1 | 1 | 0.1 |
| 14 | 7.19 | 1847.8 | ND | ND | 0.1 | 0.1 | 1 | 0.1 |

In Table 1, detection limits (fmol/well) of a mixture of fourteen kinds of peptides using ATHAP (C8-ATHAP), ATHAP+CHCA (C8-ATHAP+4-CHCA) (10+1), and CHCA (4-CHCA) are shown in descending order according to hydrophobicity of peptide. As a result, when ATHAP was used solely, several hydrophilic peptides were not detected (ND), and when CHCA was used solely, several hydrophobic peptides were not detected (ND). In contrast to these results, when a mixed matrix ATHAP+CHCA (10+1) was used, all the peptide samples Nos. 1 to 14 (SSRCalc Hydrophobicity: 7.19 to 54.76) ranging from hydrophilic to hydrophobic were detected. Further, by using ATHAP+CHCA (10+1), the sensitivity to every peptide sample was comparable or improved not less than 10 to 100 folds, compared with the case of using ATHAP solely or CHCA solely. In Table 1, the case of S/N<2 is indicated by "ND" that means "not detected".

FIG. 3 show MS imaging of NF-kB Inhibitor (SSRCalc Hydrophobicity: 54.76) which is relatively highly hydrophobic, and Amyloid β 1-11 (SSRCalc Hydrophobicity: 13.47) which is relatively hydrophilic, when ATHAP, ATHAP+4-CHCA (10+1), and 4-CHCA were respectively used.

The result verified that when a mixed matrix ATHAP+4-CHCA (10+1) was used, ions of the hydrophobic peptide were detected in the entire area of the interior of the crystal, and ions of the hydrophilic peptide were detected in the outer edge part. Accordingly, we supposed the possibility that the suppressing effect or the concentrating effect of the sample by separation between hydrophobic peptides and hydrophilic peptides influences on the improvement in coverage and sensitivity. Further, this separating effect enables selection of the laser irradiation position and enables rapid analysis. In FIG. 3, the case of S/N<2 is indicated by "ND" that means "not detected".

What is claimed is:

1. A MALDI mass spectrometry method for analyzing a sample using as a mixed matrix,

2,4,6-trihydroxyalkylphenone represented by the following general formula (I):

wherein R represents an alkyl group having 3 to 12 carbon atoms, and a matrix (II) for mass spectrometry that is more hydrophilic than 2,4,6-trihydroxyalkylphenone represented by the formula (I) wherein R is an alkyl group having 3 carbon atoms.

2. The mass spectrometry method according to claim 1, wherein the compound represented by the general formula (I) is 1-(2,4,6-trihydroxyphenyl)octan-1-one having the following structure:

3. The mass spectrometry method according to claim 1, wherein the matrix (II) for mass spectrometry is selected from the group consisting of α-cyano-4-hydroxycinnamic acid (4-CHCA), 2,5-dihydroxybenzoic acid (DHB), and 2,4,6-trihydroxyacetophenone (THAP).

4. The mass spectrometry method according to claim 1, wherein a hydrophobic focus plate is used.

5. The mass spectrometry method according to claim 1, wherein a sample to be analyzed is a mixture sample containing a peptide and a compound other than peptide.

6. The mass spectrometry method according to claim 1, wherein the sample to be analyzed is a mixture sample containing a plurality of peptides having different hydrophobicity. The term peptide includes protein.

7. The mass spectrometry method according to claim 1, wherein the sample to be analyzed is a mixture sample containing a protein digest.

* * * * *